US00PP35419P2

(12) United States Plant Patent
Van Swieten

(10) Patent No.: US PP35,419 P2
(45) Date of Patent: Oct. 10, 2023

(54) ***PHALAENOPSIS* ORCHID PLANT NAMED 'PHA227444'**

(50) Latin Name: ***Phalaenopsis* hybrid**
Varietal Denomination: PHA227444

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 18/445,050

(22) Filed: Mar. 17, 2023

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — Jondle & Associates, P.C.

(57) ABSTRACT

A new and distinct variety of *Phalaenopsis* plant named 'PHA227444', particularly characterized by having small copper, striped flowers with red-purple lips, flowers that are concave in lateral view, apical lobes of lips have a bump and ridge, and is propagated by meristem tissue culture, is disclosed.

3 Drawing Sheets

Genus and species: *Phalaenopsis* hybrid.
Variety denomination: 'PHA227444'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA227444'.

The new *Phalaenopsis* plant is a product of a planned breeding program conducted by the inventor in Bleiswijk, the Netherlands. The objective of this breeding program was to create a new *Phalaenopsis* plant with numerous small, copper, striped flowers with red-purple lips, suitable for potted plant production.

The new *Phalaenopsis* plant 'PHA227444' is a result of cross-pollination made by the inventor in March 2014 in Bleiswijk, the Netherlands, of the proprietary female, or seed parent, *Phalaenopsis* hybrid '08-040704-0003' (unpatented) with the proprietary male, or pollen parent, *Phalaenopsis* hybrid 'PHALFUEOZ' (U.S. Plant Pat. No. 30,313).

The new *Phalaenopsis* was selected by the inventor as a single plant within the progeny of the stated cross-pollination in a controlled greenhouse in Bleiswijk, the Netherlands, in November 2016. Asexual reproduction of the new *Phalaenopsis* plant by meristem tissue culture since 2017 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 15, 2021 (Application no. 2021/2277), by Applicant who obtained the subject matter disclosed directly from the inventor. 'PHA227444' has not been made publicly available or sold anywhere in the world prior to the effective filing date of this application with the exception of sales or disclosures made one year or less before the effective filing date of this claimed invention by Applicant who obtained 'PHA227444' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA227444' as a new and distinct variety of *Phalaenopsis* plant:

1) Small, copper, striped flowers with red-purple lips;
2) Flower shape in lateral view is concave; and
3) Apical lobes of the lips have a bump and ridge.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in January 2023. Colors in the photographs may differ from the color values cited in the detailed botanical description, which accurately describe the actual colors of the new variety.

DESCRIPTION OF THE NEW VARIETY

Figure 1:
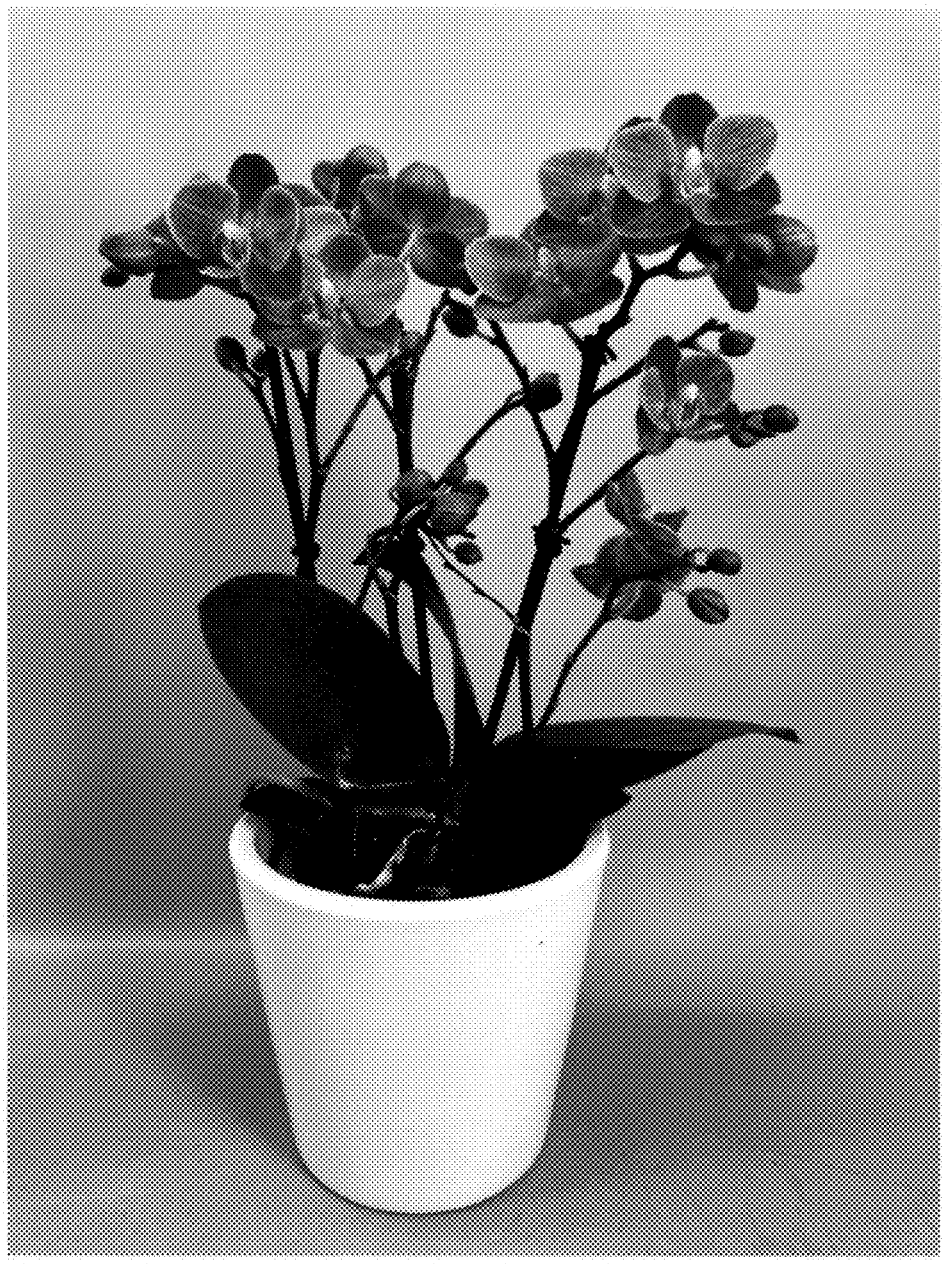
FIG. 1 shows the overall plant habit, including blooms, buds, and foliage of 'PHA227444'.
Figure 2:
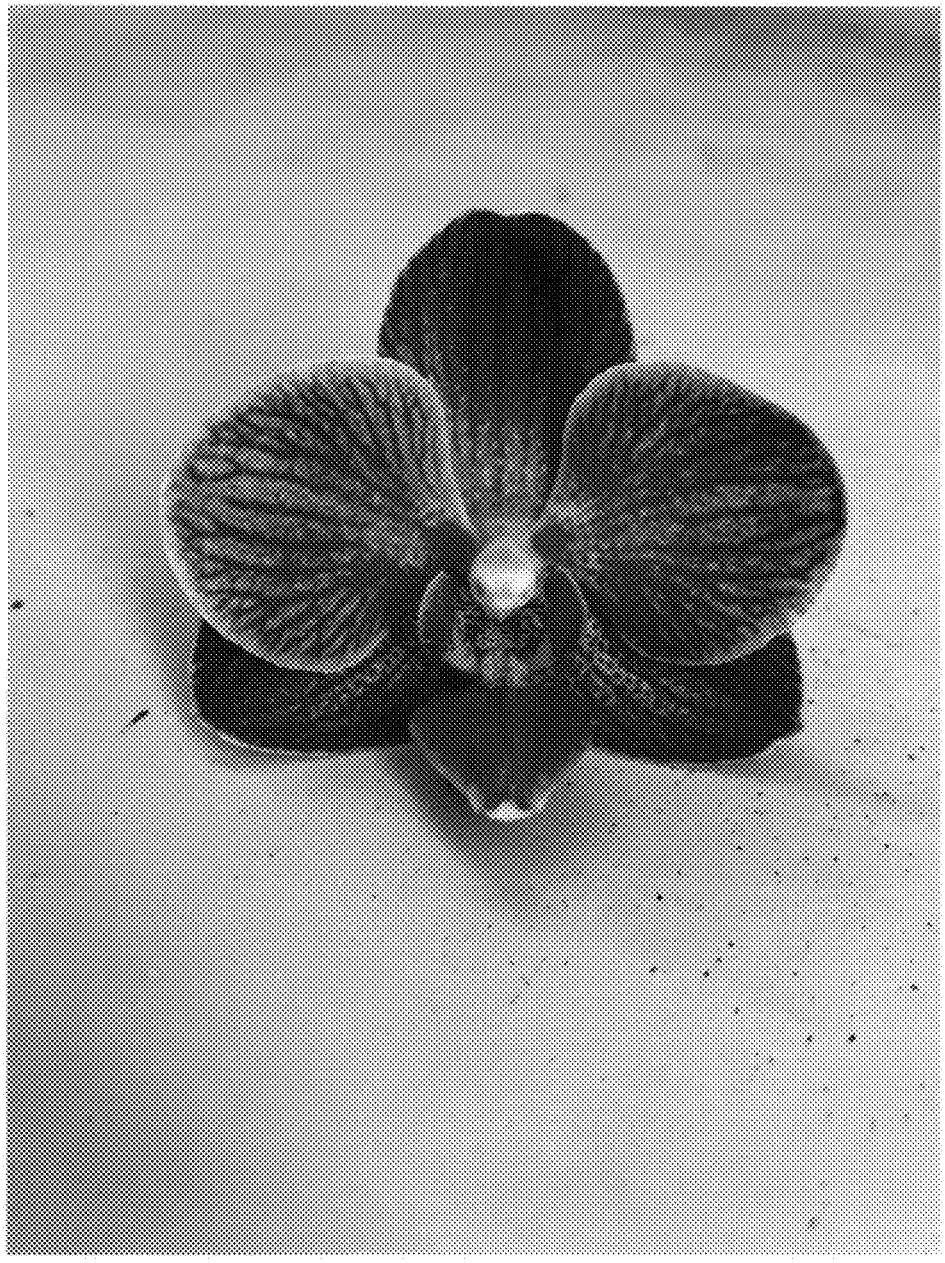
FIG. 2 shows a close-up of a flower of 'PHA227444'.
Figure 3:
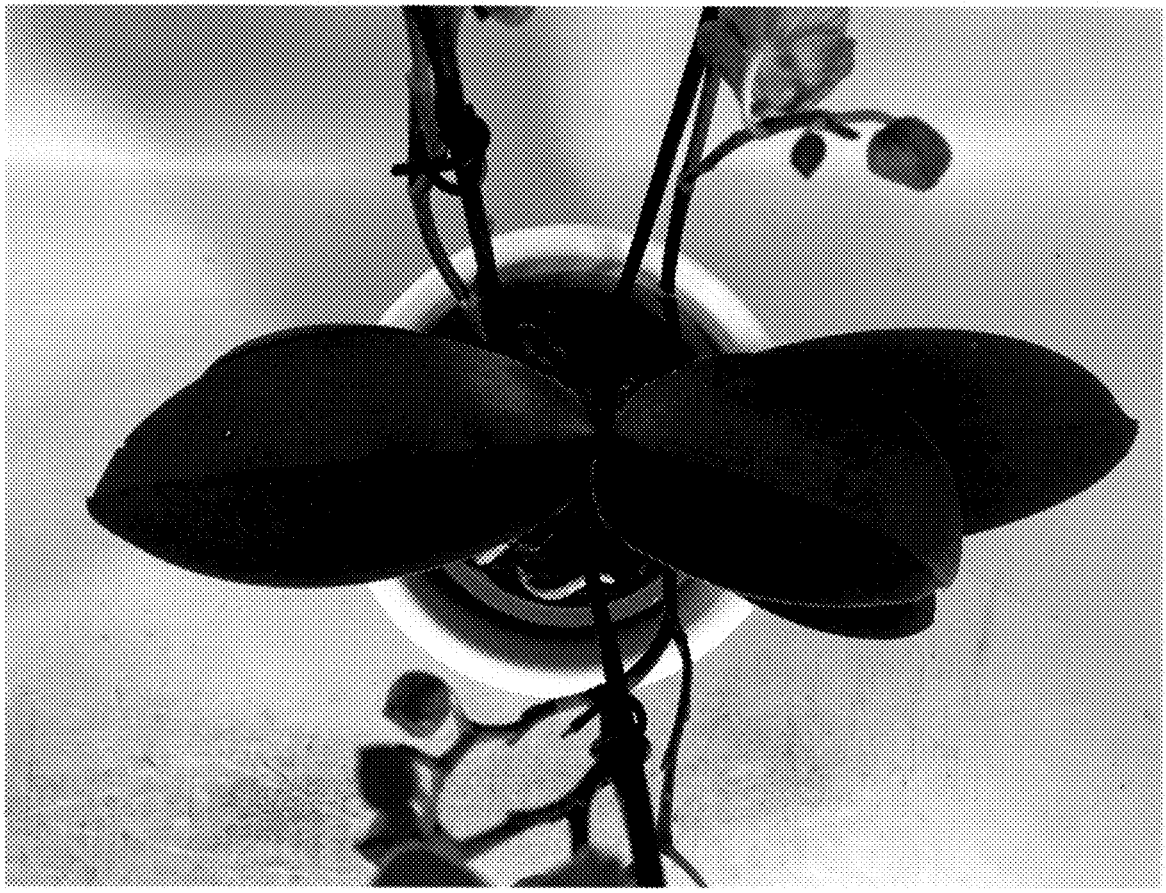
FIG. 3 shows an overhead, close-up view of the leaves of 'PHA227444'.

The following detailed description sets forth the distinctive characteristics of 'PHA227444'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in January 2023 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHA227444'.

Parentage:

*Female parent*.—*Phalaenopsis* cultivar '08-040704-0003' (unpatented).

*Male parent*.—*Phalaenopsis* cultivar 'PHALFUEOZ' (U.S. Plant Pat. No. 30,313).

Propagation:

*Type*.—Meristem tissue culture.

Roots:

*Root description*.—Greyed-green (a color in between RHS 190B and RHS 190C) colored roots with branching lateral roots having yellow-green (RHS 144C) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with panicle inflorescence.

*Height* (*from soil level to top of inflorescence*).—Approximately 27.0 cm to 33.0 cm.

*Width* (*measured from leaf tips*).—About 25.0 cm to 27.0 cm.

*Vigor*.—Strong.

Leaves:

*Mature leaves*.—Quantity per plant: 9 to 11 leaves are produced before flowering. Length (fully expanded): 11.0 cm to 14.0 cm. Width: 6.0 cm to 7.0 cm. Position of the broadest part of the leaf: At the middle. Shape: Oblong. Base shape: Slightly elongated. Apex: Obtuse asymmetric. Leaf blade angle with the petiole (measured from the horizontal position): Between 15 degrees and 30 degrees. Leaf margin: Entire. Color: Upper surface: Green (RHS 147A). Lower surface: Green (RHS 147B) with a dark red margin (RHS N186C) toward the tip. Texture (both upper and lower surfaces): Smooth. Thickness: 2.0 mm to 3.0 mm. Variegation: Absent. Venation: Pattern: Parallel. Color of the midvein: Upper surface: Green (RHS 147A). Lower surface: Green (RHS 147B).

Peduncle:

*Quantity per plant*.—2 to 4.

*Number of flowers per peduncle*.—11 to 17.

*Length*.—27.0 cm to 33.0 cm.

*Diameter*.—3.0 mm to 4.0 mm.

*Strength*.—Strong.

*Aspect*.—Upright to slightly pendent.

*Texture*.—Smooth.

*Color*.—A mix of green (RHS 147C) and dark brown (RHS N200A).

*Internode length*.—1.5 cm to 2.0 cm.

Inflorescence description:

*Appearance*.—Upright to slightly pendent, panicle inflorescence with bilaterally symmetrical flowers that open in succession beginning with the lowermost flower.

*Number of inflorescences*.—2 to 4.

*Inflorescence size*.—Height (from base to tip): 160.0 mm to 220.0 mm.

*Flowering time*.—First flowers can be expected 10 to 11 months after planting in a 12-cm pot.

*Flower*.—Height: 45.0 mm to 50.0 mm. Diameter: 50.0 mm to 55.0 mm. Depth of lip: 14.0 mm to 16.0 mm.

*Flower shape*.—Concave.

*Flower longevity*.—On the plant: 9 to 11 weeks.

*Fragrance*.—Absent.

*Flower bud*.—Average size: Medium. Length: 17.0 mm to 19.0 mm. Width: 15.0 mm to 17.0 mm. Shape: Egg shaped. Color: Dark greenish-yellow (RHS 152D) with dark red shade (RHS 187C) and purplish-red stripes (RHS N77B).

*Petals*.—Arrangement: Open/free. Shape: Semi-circular. Apex: Rounded asymmetric. Margin: Weakly undulated. Length (from base to tip): 23.0 mm to 25.0 mm. Width: 20.0 mm to 22.0 mm. Position of the broadest part of the petal: Toward the base. Color (when fully opened): Upper surface: Basic color: Light greenish-yellow (RHS 160C). Over color: Purplish-red (RHS 184C), purplish-red stripes (RHS 71A), and very small purplish-red dots (RHS 64B) at the base. Lower surface: Basic color: Light greenish-yellow (RHS 160C). Over color: Diluting purplish-red stripes (RHS 70B). Number of spots and stripes on the petals (upper surface): Few dots and many stripes. Color of spots and stripes on the petals (upper surface): Dots RHS 64B and stripes RHS 71A. Density of netting of the petals (upper surface): Low. Color of the netting (upper surface): RHS 71A.

*Dorsal sepal*.—Shape: Elliptic. Apex: Emarginated symmetric. Margin: Entire. Length (from base to tip): 26.0 mm to 28.0 mm. Width: 21.0 mm to 23.0 mm. Position of the broadest part of the dorsal sepals: At the middle. Color (when fully opened): Upper surface: Basic color: Light greenish-yellow (RHS 160C). Over color: Touch of light reddish-purple (RHS NN74C) at the base; red-purple stripes (RHS 72A), and netting RHS 64B; very small dots RHS 162C, and red shade (RHS 185B) toward the tips. Lower surface: Basic color: Light greenish-yellow (RHS 160C). Over color: Touch of purplish-pink (RHS 186D) at the base and dark greenish-yellow (RHS 152C) at the middle toward the tip;

diluting purplish-red stripes (RHS 186A) and pink shade (RHS 185D) toward margin. Number of spots and stripes on the dorsal sepals (upper surface): Medium very small dots and medium stripes. Color of spots and stripes on the dorsal sepals (upper surface): Dots RHS 162C and stripes RHS 72A. Density of netting of the dorsal sepals (upper surface): Low. Color of the netting (upper surface): RHS 64B.

*Lateral sepals*.—Shape: Ovate. Apex: Obtuse asymmetric. Margin: Entire. Length (from base to tip): 26.0 mm to 28.0 mm. Width: 21.0 mm to 23.0 mm. Position of the broadest part of the lateral sepals: Toward the base. Color (when fully opened): Upper surface: Basic color: Light yellow (RHS 162C). Over color: Greenish-yellow (RHS 151C) and dotted RHS 59B at the base; purplish-red shade (RHS 186A) toward one margin and the tip, and stripes RHS 71A. Lower surface: Basic color: Light greenish-yellow (RHS 160C). Over color: Purplish-red shade (RHS 186B) at the margin and diluting reddish-purple stripes (RHS 186A). Number of spots and stripes on the lateral sepals (upper surface): May very small dots and medium stripes. Color of spots and stripes on the lateral sepals (upper surface): Dots RHS 59B; stripes RHS 71A. Density of netting of the lateral sepals (upper surface): Low. Color of the netting (upper surface): RHS 71A.

*Labellum* (*lip*).—Whiskers: Present, but very short. Length of whiskers: About 1.0 mm. Color of whiskers: Light greenish-yellow (RHS 2D). Pubescence on the lip: Absent.

*Lateral lobe*.—Shape: Type III (as described in the International Union for the Protection of New Varieties of Plants (UPOV) Test Guidelines for *Phalaenopsis*); oblong. Margin: Slightly undulated. Length: 10.0 mm to 12.0 mm. Width: 4.0 mm to 6.0 mm. Color: Upper surface: Yellow (RHS 162B) at the base with a touch of yellow (RHS 12A); purplish-red stripes (RHS 59B); reddish-purple (RHS 72B) toward tips. Lower surface: Touch of light yellow (RHS 160D) at the base; yellow margin on one side (RHS 12A); red on one side (RHS 185A) and reddish-purple (RHS 72B) toward the tip. Number of spots and stripes on the lateral lobe: Medium stripes. Color of spots and stripes on the lateral lobe: RHS 59B. Density of netting of the lateral lobe: None. Color of the netting: None.

*Apical lobe*.—Shape: Trullate. Margin: Entire. Length: 14.0 mm to 16,0 mm. Width: 14.0 mm to 16.0 mm. Color: Upper surface: Touch of yellow (RHS 15B) and very small red spots (RHS 185A) at the base; dark purplish-red midvein (RHS 187D); purplish-red (RHS 60C) with a touch of reddish-purple (RHS NN78A) toward whiskers. Lower surface: Touch of orange-yellow (RHS 163B) at the base; light yellow (RHS 162D) at the middle; diluting purplish-red stripes (RHS 70A) and shade RHS 186B toward margins. Number of spots and stripes on the apical lobe: Very many, very small spots. Color of spots and stripes on the apical lobe: RHS 185A. Density of netting of the apical lobe: None. Color of the netting: None. Bump and ridge: Present.

*Callus*.—Average size: Small. Height: 2.0 mm to 3.0 mm. Length: 2.0 mm to 3.0 mm. Width: 1.0 mm to 2.0 mm. Color: Light yellow (RHS 8B) on sides, front, and backside; yellow tips (RHS 14A) and purplish-red dots (RHS 59B).

Reproductive organs:

*Column*.—Length: 8.0 mm to 9.0 mm. Diameter: 4.0 mm to 5.0 mm. Color: Very light purple (RHS 76B) and touch of light reddish-purple (RHS N78D) at the base and tip.

*Pollinia*.—Quantity: 2. Diameter: 0.6 mm to 0.8 mm. Color: Orange-yellow (RHS 23A).

*Ovary*.—Length: 7.0 mm to 9.0 mm. Diameter: 1.7 mm to 1.9 mm.

*Pedicel*.—Length: 26.0 mm to 28.0 mm. Diameter: 1.9 mm to 2.1 mm. Color: Light yellow-green (RHS 145A) at the base; lighter yellow-green (a color between RHS 145C and RHS 145D) with a touch of very light purple (RHS 76C) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA227444' differs from the female parent plant '08-040704-0003' (unpatented) in that 'PHA227444' has spotted apical lobes and light greenish-yellow flowers, whereas '08-040704-0003' has striped apical lobes and very light purple flowers.

'PHA227444' differs from the male parent plant 'PHALFUEOZ' (U.S. Plant Pat. No. 30,313) in that 'PHA227444' has concave, light greenish yellow flowers and yellow calluses, whereas 'PHALFUEOZ' has convex, dark red flowers and dark red calluses.

'PHA227444' is most similar to the commercial *Phalaenopsis* plants named 'PHALGUAJO' (U.S. Plant Pat. No. 32,145) and 'PHALIFQUDI' (U.S. Plant Pat. No. 26,831), 'PHA227444' differs from the commercial variety 'PHALGUAJO' in that 'PHA227444' has trullate apical lobes, incurving longitudinal axis, and light greenish-yellow whiskers. whereas 'PHALGUAJO' has elliptic apical lobes, recurving longitudinal axis, and white dotted whiskers.

'PHA227444' differs from the commercial variety 'PHALIFQUDI' in that 'PHA227444' has very short, light greenish-yellow whiskers and oblong lateral lobes, whereas 'PHALIFQUDI' has short to medium, dark purplish-red with small yellow tipped whiskers and spatulated lateral lobes.

I claim:

1. A new and distinct variety of *Phalaenopsis* plant named 'PHA227444', substantially as described and illustrated herein.

* * * * *